US00PP35501P2

(12) United States Plant Patent
Tashiro

(10) Patent No.: US PP35,501 P2
(45) Date of Patent: Nov. 21, 2023

(54) ***LOBELIA* PLANT NAMED 'BALWATARLU'**

(50) Latin Name: *Lobelia erinus*
Varietal Denomination: Balwatarlu

(71) Applicant: Ball Horticultural Company, West Chicago, IL (US)

(72) Inventor: Rebecca M. Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/123,822

(22) Filed: Mar. 20, 2023

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Lobelia* plant named 'Balwatarlu', characterized by its dark violet-blue colored flowers having a white eye, medium green colored foliage, and vigorous, mounded, semi-trailing growth habit, is disclosed.

1 Drawing Sheet

Latin name of genus and species of plant claimed: *Lobelia erinus*.

Variety denomination: 'Balwatarlu'.

BACKGROUND OF THE INVENTION

The present invention relates to a new and distinct cultivar of *Lobelia* plant botanically known as *Lobelia erinus* and hereinafter referred to by the cultivar name 'Balwatarlu'.

The new cultivar originated in a controlled breeding program in Guadalupe, California during October 2017. The objective of the breeding program was the development of heat tolerant *Lobelia* cultivars having a long flowering season with a vigorous, mounded, semi-trailing growth habit suitable for baskets.

The new *Lobelia* cultivar is the result of cross-pollination. The female (seed) parent of the new cultivar is TECHNO Heat Upright Blue 'LOBZ0011', U.S. Plant Pat. No. 28,868, characterized by its large, medium blue-colored flowers having a white eye, medium green-colored foliage, and vigorous, upright growth habit. The male (pollen) parent of the new cultivar is TECHNO Heat Dark Blue 'Tech Hepdab', U.S. Plant Pat. No. 21,049, characterized by its deep blue-colored flowers having a white eye, dark green-colored foliage, and moderately vigorous, mounded growth habit. The new cultivar was selected as a single flowering plant within the progeny of the above stated cross-pollination during April 2018 in a controlled environment in Guadalupe, California.

Asexual reproduction of the new cultivar by terminal stem cuttings since April 2018 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balwatarlu' as a new and distinct cultivar of *Lobelia* plant:

1. Dark violet-blue colored flowers having a white eye;
2. Medium green colored foliage; and
3. Vigorous, mounded, semi-trailing growth habit.

Plants of the new cultivar differ from plants of the female parent primarily in having darker violet-blue colored flowers and a more trailing growth habit. Plants of the new cultivar differ from plants of the male parent primarily in having increased growth vigor and a more trailing growth habit.

Of the many commercially available *Lobelia* cultivars, the most similar in comparison to the new cultivar is Waterfall Blue 'Balobwablu', U.S. Plant Pat. No. 16,524. However, in side-by-side comparison, plants of the new cultivar differ from plants of 'Balobwablu' in at least the following characteristics:

1. Plants of the new cultivar have slightly lighter violet-blue colored flowers than plants of 'Balobwablu'; and
2. Plants of the new cultivar have a larger calyx than plants of 'Balobwablu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balwatarlu'. The plants were approximately 13-weeks old. The plants were grown in 4.5-inch containers for approximately 9 weeks in a greenhouse in West Chicago, Illinois. Plants were given two pinches, one at transplant and one three weeks after transplant.

DETAILED BOTANICAL DESCRIPTION

Figure 1:
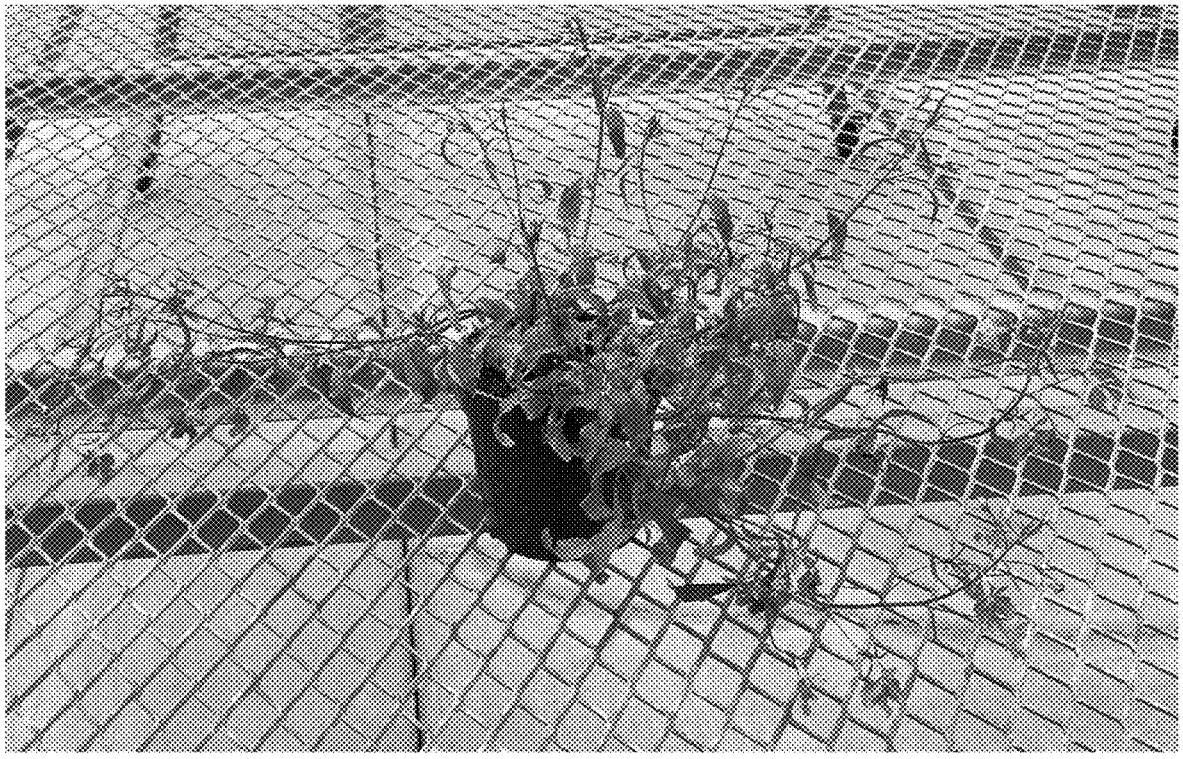
FIG. 1 illustrates a side view of the overall growth and flowering habit of 'Balwatarlu'.
Figure 2:
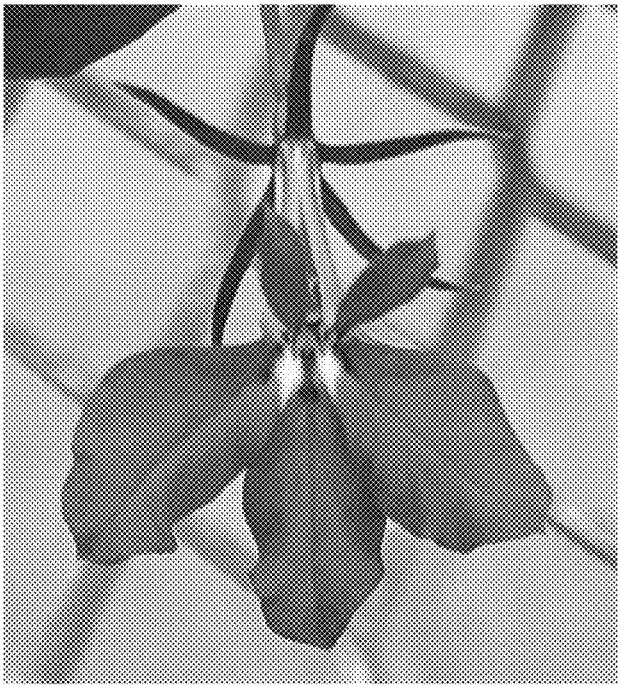
FIG. 2 illustrates a close-up view of the inflorescences of 'Balwatarlu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2023 under natural light conditions in Naperville, Illinois.

The following descriptions and measurements describe approximately 13-week-old plants produced from cuttings from stock plants and grown in a polycarbonate greenhouse under conditions comparable to those used in commercial practice. The plants were grown in West Chicago, Illinois in 4.5-inch containers for approximately 9 weeks utilizing a soilless growth medium. Plants were given two pinches, one at transplant and one three weeks after transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Lobelia erinus* 'Balwatarlu'.

Parentage:

*Female parent.*—TECHNO Heat Upright Blue 'LOBZ0011', U.S. Plant Pat. No. 28,868.

*Male parent.*—TECHNO Heat Dark Blue 'Tech Hepdab', U.S. Plant Pat. No. 21,049.

Propagation:

*Type cutting.*—Terminal stem.

*Time to initiate roots.*—Approximately 6 to 9 days.

*Time to produce a rooted cutting.*—Approximately 4 to 5 weeks.

*Root description.*—Fine to medium, fibrous.

*Rooting habit.*—Freely branching.

Plant description:

*Commercial crop time.*—Approximately 9 to 10 weeks from a rooted cutting to finish in a 10 cm container.

*Growth habit and general appearance.*—Vigorous, mounded, semi-trailing.

*Size.*—Height from soil level to top of plant plane: Approximately 17.5 cm. Width: Approximately 54.0 cm.

*Branching habit.*—Freely branching, pinching enhances lateral branching. Quantity of branches per plant: Approximately 6 main branches with approximately 2 to 4 lateral branches per main branch.

*Lateral branch.*—Shape: Square in cross section. Strength: Strong, flexible. Length: Approximately 20.0 cm. Diameter: Approximately 2.0 mm to 3.0 mm. Length of central internode: Approximately 2.8 cm. Texture: Sparsely pubescent. Color of young stems: 146A. Color of mature stems: 137A.

Foliage description:

*General Description.*—Quantity of leaves per branch: Approximately 8. Fragrance: None detected. Form: Simple. Arrangement: Alternate.

*Leaves.*—Aspect: Acute angle to stem with tips downward turning. Shape: Narrowly elliptic. Margin: Shallowly serrate, sparsely ciliate. Apex: Acute. Base: Sessile. Venation pattern: Pinnate. Length of mature leaf: Approximately 4.0 cm. Width of mature leaf: Approximately 1.2 cm. Texture of upper surface: Glabrous. Texture of lower surface: Sparsely pubescent. Color of upper surface of young and mature foliage: 137A with venation of 137B. Color of lower surface of young and mature foliage: 138B with venation of 138A.

Flowering description:

*Flowering habit.*—'Balwatarlu' is freely flowering under outdoor conditions with substantially continuous blooming from early spring through autumn and year-round in a greenhouse environment.

Inflorescence description:

*General description.*—Type: Loose raceme. Quantity per plant: Approximately 11. Fragrance: None detected. Length or height of inflorescence: Approximately 8.5 cm to 13.5 cm. Width of inflorescence: Approximately 6.0 cm to 8.0 cm. Quantity of fully-open flowers per inflorescence: Approximately 3 to 8.

Flower description:

*Type.*—Single, zygomorphic, bilabiate.

*Bud just before opening.*—Shape: Oblanceolate. Length: Approximately 1.0 cm. Diameter at distal end: Approximately 4.0 mm. Diameter at proximal end: Approximately 2.0 mm. Texture: Glabrous. Color: 145B.

*Corolla.*—Shape: Bilabiate having an upper lip of two narrow lobes and a lower lip of three lobes. Lobes are fused at the base forming a tube that is split between the two upper lobes. Aspect: Facing upward and outward ad occasionally downward. Width: Approximately 2.2 cm. Length: Approximately 2.0 cm. Depth: Approximately 1.5 cm.

*Upper lobes.*—Shape: Oblanceolate. Margin: Entire, ciliate. Apex: Mucronate. Length from throat: Approximately 9.0 mm. Width: Approximately 3.0 mm. Texture of upper (inner) surface: Sparsely pubescent near base. Texture of lower (outer) surface: Glabrous. Color of upper (inner) surface when first open: Closest to 94A. Color of lower (outer) surface when first open: Slightly lighter than 94B. Color of upper (inner) surface when fully open: Closest to slightly lighter than 94A. Color of lower (outer) surface when fully open: Slightly lighter than 94B.

*Lower lobes.*—Shape: Obovate. Margin: Entire, ciliate at base. Apex: Mucronate to rounded. Length from throat: Approximately 1.3 cm. Width: Approximately 9.0 mm. Texture of upper (inner) surface: Sparsely pubescent near base. Texture of lower (outer) surface: Sparsely pubescent. Color of upper (inner) surface when first open: Closest to 94A with basal margins of NN155D. Color of lower (outer) surface when first open: 94C to 94D. Color of upper (inner) surface when fully open: Closest to slightly lighter than 94A with basal margins of NN155D. Color of lower (outer) surface when fully open: 94C to 94D.

*Corolla tube.*—Length: Approximately 9.0 mm. Width at opening: Approximately 5.0 mm. Width at base: 2.0 mm. Texture of inner surface: Glabrous with sparse pubescence at throat opening. Texture of outer surface: Glabrous. Color of inner surface: NN155D with two zigzag stripes of 94B near the throat opening and two faint nectary tracks of 144A. Color of outer surface: Slightly lighter than 94B with 94D.

*Calyx.*—Shape: Star. Length: Approximately 1.5 cm. Diameter: Approximately 1.7 cm.

*Sepals.*—Quantity per flower: 5. Shape: Lanceolate. Margin: Entire, ciliate. Apex: Acute. Base: Fused into cup-like structure. Length of free portion: Approximately 1.1 cm. Width: Approximately 1.0 mm. Texture of inner and outer surface: Glabrous. Color of inner and outer surfaces: 137A.

*Pedicel.*—Strength: Strong, flexible. Aspect: At an acute angle, occasionally curled. Length: Approximately 2.0 cm to 3.0 cm. Diameter: Approximately 1.0 mm Texture: Glabrous. Color: 137A.

*Reproductive organs.*—Androecium: Stamen quantity: 5 per flower, upper half of filaments connate. Stamen length: Approximately 8.0 mm. Filament color: 94C to 94D. Anther shape: Oblong. Anther length: Approximately 2.0 mm. Anther color: N92C. Pollen amount: None observed. Gynoecium: Pistil quantity: 1 per flower. Pistil length: Approximately 1.3 cm. Stigma shape: Bilobate. Stigma length: Approximately 1.0 mm. Stigma color: N92B. Style length: Approximately 8.0 mm. Style color: 144A. Ovary length: Approximately 4.0 mm. Ovary color: 137A.

Seed and fruit production: Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balwatarlu', substantially as herein illustrated and described.

* * * * *